(12) United States Patent
Kuramochi

(10) Patent No.: US 10,258,513 B2
(45) Date of Patent: Apr. 16, 2019

(54) ABSORBENT ARTICLE

(71) Applicant: DAIO PAPER CORPORATION, Shikokuchuo-shi, Ehime (JP)

(72) Inventor: Mihoko Kuramochi, Sakura (JP)

(73) Assignee: DAIO Paper Corporation, Ehime (JP)

( * ) Notice: Subject to any disclaimer, the term of this patent is extended or adjusted under 35 U.S.C. 154(b) by 224 days.

(21) Appl. No.: 15/039,239

(22) PCT Filed: Nov. 20, 2014

(86) PCT No.: PCT/JP2014/080780
§ 371 (c)(1),
(2) Date: May 25, 2016

(87) PCT Pub. No.: WO2015/076337
PCT Pub. Date: May 28, 2015

(65) Prior Publication Data
US 2016/0361210 A1 Dec. 15, 2016

(30) Foreign Application Priority Data
Nov. 25, 2013 (JP) .................................. 2013-242628

(51) Int. Cl.
| | |
|---|---|
| *A61F 13/15* | (2006.01) |
| *A61F 13/47* | (2006.01) |
| *A61F 13/472* | (2006.01) |
| *A61F 13/476* | (2006.01) |
| *A61F 13/514* | (2006.01) |
| *A61F 13/515* | (2006.01) |

(Continued)

(52) U.S. Cl.
CPC ........ *A61F 13/4704* (2013.01); *A61F 13/476* (2013.01); *A61F 13/47236* (2013.01); *A61F 13/515* (2013.01); *A61F 13/51401* (2013.01); *A61F 13/51474* (2013.01); *A61F 13/539* (2013.01); *A61F 13/5616* (2013.01); *A61F 2013/51143* (2013.01); *A61F 2013/51147* (2013.01); *A61F 2013/51488* (2013.01); *A61F 2013/5395* (2013.01)

(58) Field of Classification Search
CPC ............ A61F 13/4704; A61F 13/47236; A61F 13/476; A61F 13/51401; A61F 13/51474; A61F 13/515; A61F 13/539; A61F 13/5616
USPC ..................................................... 604/385.04
See application file for complete search history.

(56) References Cited

FOREIGN PATENT DOCUMENTS

| | | |
|---|---|---|
| JP | 2003-111799 | 4/2003 |
| JP | 2004-113590 | 4/2004 |

(Continued)

*Primary Examiner* — Jacqueline Stephens
(74) *Attorney, Agent, or Firm* — Norris McLaughlin, P.A.

(57) ABSTRACT

A wing-shaped flap has a front side outline extending outward from a main body, a back side outline which extends outward from the main body and a tip end side outline which connects the front side outline and the back side outline. The tip end side outline includes a tip end side outline front portion extending outward from an end portion of the front side outline and a tip end side outline back portion extending outward from an end portion of the back side outline, and an intersection between the tip end side outline front portion and the tip end side outline back portion forms an outermost side end portion in a width direction of the wing-shaped flap and is located on a front side with respect to a center point of a length between the end portion of the front side outline and the end portion of the back side outline in a longitudinal direction of an absorbent article.

4 Claims, 9 Drawing Sheets

(51) Int. Cl.
*A61F 13/539* (2006.01)
*A61F 13/56* (2006.01)
*A61F 13/511* (2006.01)

(56) References Cited

FOREIGN PATENT DOCUMENTS

| | | |
|---|---|---|
| JP | 2008-012098 | 1/2008 |
| JP | 2013-176695 | 9/2013 |
| JP | 2013-220225 | 10/2013 |

ABSORBENT ARTICLE

BACKGROUND OF THE INVENTION

The present invention relates to an absorbent article provided with wing-shaped flaps which are used so as to be wrapped around the crotch part of underwear when the absorbent article is fixed to the underwear.

Conventionally, as an absorbent article N such as a sanitary napkin, a panty liner, a vaginal discharge sheet or an incontinence pad, for example, as shown in FIG. 10, an absorbent article is known in which an absorbent member 52 formed of cotton-like pulp or the like is interposed between a liquid impermeable back sheet 50 formed with a polyethylene sheet, a polyethylene-laminated nonwoven fabric or the like and a liquid permeable front sheet 51 formed with a nonwoven fabric, a porous plastic sheet or the like.

As this type of absorbent article N, an absorbent article is present in which in order to prevent displacement in a fitted state, for example, one or a plurality of strips of adhesive layers 53 are formed on a non-skin contact surface (outer surface), in which on both side portions of a napkin main body in a longitudinal direction, wing-shaped flaps W extending outward are integrally formed and in which adhesive layers 54 are provided on the surfaces (outer surfaces) of the wing-shaped flaps W on the side of the liquid impermeable back sheet 50 (see Japanese Unexamined Patent Application Publication No. 2003-111799 and Japanese Unexamined Patent Application Publication No. 2004-113590 and the like).

In order to fix the absorbent article N to underwear 60, as shown in FIG. 11, the absorbent article N is put on a part of the underwear 60 corresponding to the part of the anatomy from which the absorbent article N is to receive excreted matter, the wing-shaped flaps W protruding laterally are protruded outward from the underwear, the wing-shaped flaps W are folded back on return lines RL and are adhered to the outer surface of the crotch portion of the underwear 60 so as to be wrapped around the crotch part of the underwear and thereafter the underwear is fitted to the body.

Many improvements have been performed on this type of absorbent article N, and for example, Japanese Unexamined Patent Application Publication No. 2008-12098 described below discloses an absorbent article in which wing portions are flexibly and easily bent along the side edge of the crotch portion of underwear and can be fixed to the underwear easily and quickly, which includes, in order for the underwear to have excellent antifouling property, an absorbent main body having an absorbing layer and a leak-proof layer and a pair of wing portions provided on both sides of the absorbent main body in an excretory portion opposite portion and in which the shapes of the pair of wing portions are asymmetric forward and backward with respect to a transversal line in a width direction passing the midpoint of the edge portion of a tip end in each of the wing portions.

SUMMARY OF THE INVENTION

Although the wing-shaped flaps W can be a significantly effective means in order to achieve the fixation to underwear, when the wing-shaped flaps W are carelessly folded back, only part thereof is folded back, the wing-shaped flaps W cannot be accurately folded back on the return lines RL and the return lines of the wing-shaped flaps are obliquely bent and folded back, with the result that for example, it is disadvantageously impossible to fix the wing-shaped flaps to the shorts.

Although in the absorbent article disclosed in patent literature 3, the wing portion is formed in a shape which has a pair of front and back edge portions (a front side outline and a back side outline) and an edge portion (a tip end side outline) of the tip end of the wind portion extending from those edge portions, the tip end side outline is formed with a straight line which is substantially parallel to the longitudinal direction of the napkin, and is formed so as to extend, in a connection part to the back side outline, in a direction substantially intersecting a tangential direction of the back side outline. Hence, when in order to fold the wing portion, an operation of putting a hand along the back side outline from a base end side toward the tip end side is performed, the hand can be moved only within a range of the back side outline and in order to move to the tip end side beyond the range, it is necessary to rapidly change the angle at which the hand is moved, with the result that it is impossible to perform an operation of continuously putting the hand therealong. Hence, disadvantageously, it is difficult to press, with the hand, the tip end side of the wing-shaped flaps, and since the tip end side is not sufficiently fixed, the wing-shaped flaps are peeled from the tip end side so as to be easily separated therefrom.

Hence, a main object of the present invention is to provide an absorbent article in which wing-shaped flaps can be securely fixed to underwear by putting a hand therealong to the tip end of the wing-shaped flaps.

In order to solve the problem described above, according to a first aspect of the present invention, there is provided an absorbent article in which on both side portions of a main body part where an absorbent member is interposed between a liquid permeable front sheet and a liquid impermeable back sheet, wing-shaped flaps are formed that are fixed so as to wrap a crotch part of underwear when being fitted, where the wing-shaped flap is formed with a front side outline which is extended outward from the main body part, a back side outline which is extended outward from the main body part and a tip end side outline which connects the front side outline and the back side outline, and the tip end side outline includes a tip end side outline front portion which is extended outward from the front side outline and a tip end side outline back portion which is extended outward from the back side outline, and an intersection between the tip end side outline front portion and the tip end side outline back portion forms an outermost side end portion in a width direction of the wing-shaped flap and is located on a front side with respect to a center point of a length between an end portion of the front side outline and an end portion of the back side outline in a longitudinal direction of the absorbent article.

In the first aspect of the invention, the planar shape of the wing-shaped flap is the shape in which the tip end side outline connecting the front side outline and the back side outline is included and in which the tip end side outline includes the tip end side outline front portion and the tip end side outline back portion, and the intersection between the tip end side outline front portion and the tip end side outline back portion forms the outermost side end portion in the width direction of the wing-shaped flap and is located on the front side with respect to the center point of the length between the end portion of the front side outline and the end portion of the back side outline in the longitudinal direction of the absorbent article. In such a shape, as will be described in detail later, when the wing-shaped flap is folded back over the substantially entire width of the wing-shaped flap from the back side outline to the tip end side outline, it is easy to fold back the wing-shaped flap by continuously putting a hand therealong to the outermost side end portion in the width direction, with the result that it is possible to securely fix the tip end side of the wing-shaped flap to the underwear.

As a second aspect of the present invention, in the absorbent article of the first aspect, the front side outline is formed with a wavy line, a curve or a combination thereof is provided.

In the second aspect of the invention, since the front side outline is formed with a wavy line, a curve or a combination thereof, and thus the rigidity of the front side of the wing-shaped flap is enhanced, the wing-shaped flap can be fitted without the occurrence of a wrinkle and a crease in the front side when the wing-shaped flap is folded back.

In the third aspect of the present invention, in the absorbent article of the first or second aspect, the tip end side outline back portion is formed with a curve, a straight line or a combination thereof.

In the third aspect of the invention, the tip end side outline back portion is formed with a curve, a straight line or a combination thereof; and thus it is possible to more smoothly put the hand therealong from the back side outline to the tip end side outline back portion when the wing-shaped flap is fixed to the underwear, with the result that the wing-shaped flap is easily fixed to the underwear.

In the fourth aspect of the present invention, the absorbent article of any one of the first to third aspects, the back side outline is formed with a straight line.

In the fourth aspect of the invention, the back side outline is formed with a straight line, and thus it is possible to easily perform the operation of putting the hand along the back side outline when the wing-shaped flap is folded back at the time of the fitting.

As described above in detail, in the present invention, it is possible to securely fix the wing-shaped flap to the underwear by putting the hand therealong to the tip end of the wing-shaped flap.

DETAILED DESCRIPTION OF THE INVENTION

An embodiment of the present invention will be described in detail below with reference to drawings.

[Structure of Sanitary Napkin 1]

Figure 1:
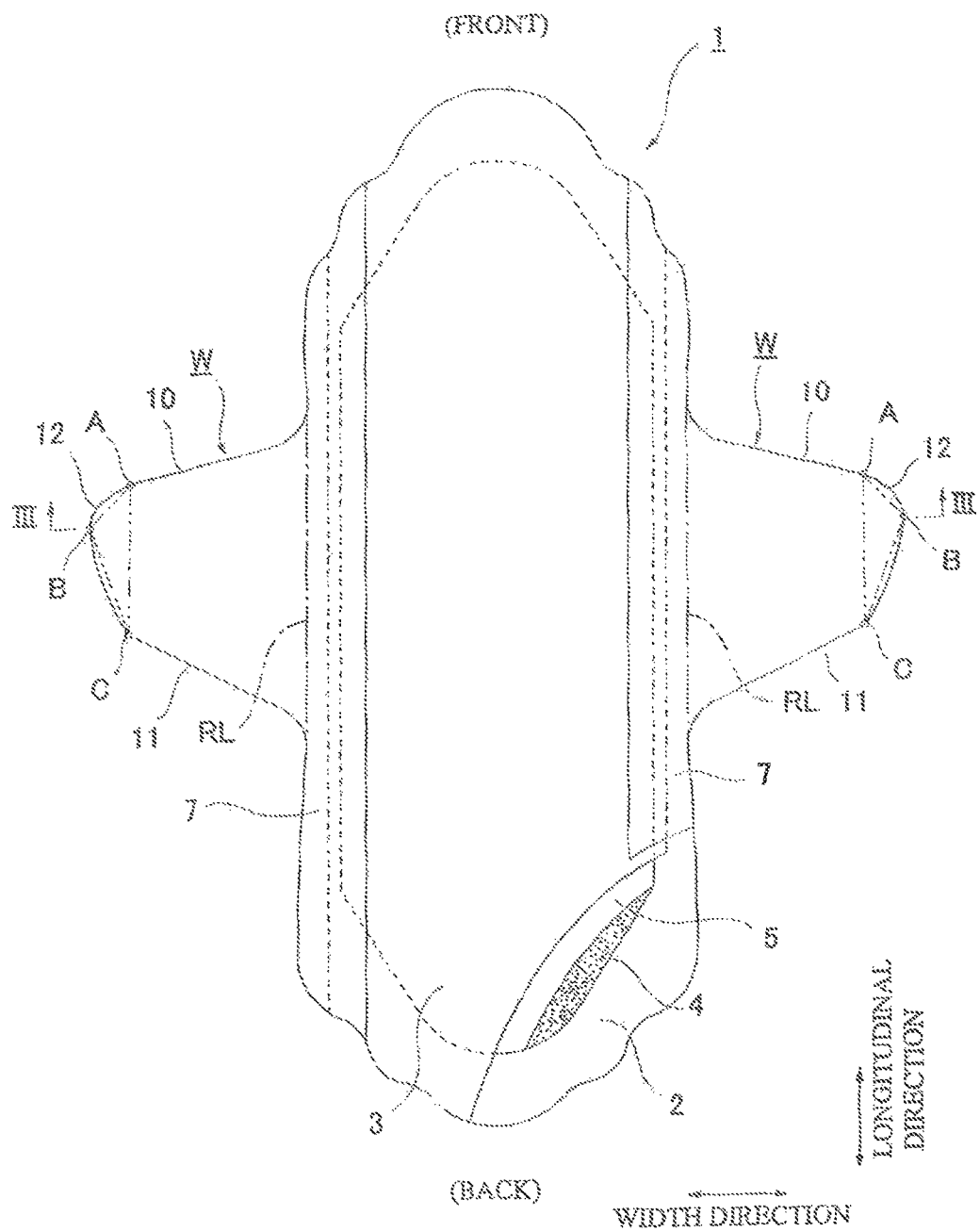
FIG. 1 is a partially broken development view of a sanitary napkin 1 according to the present invention.
Figure 2:
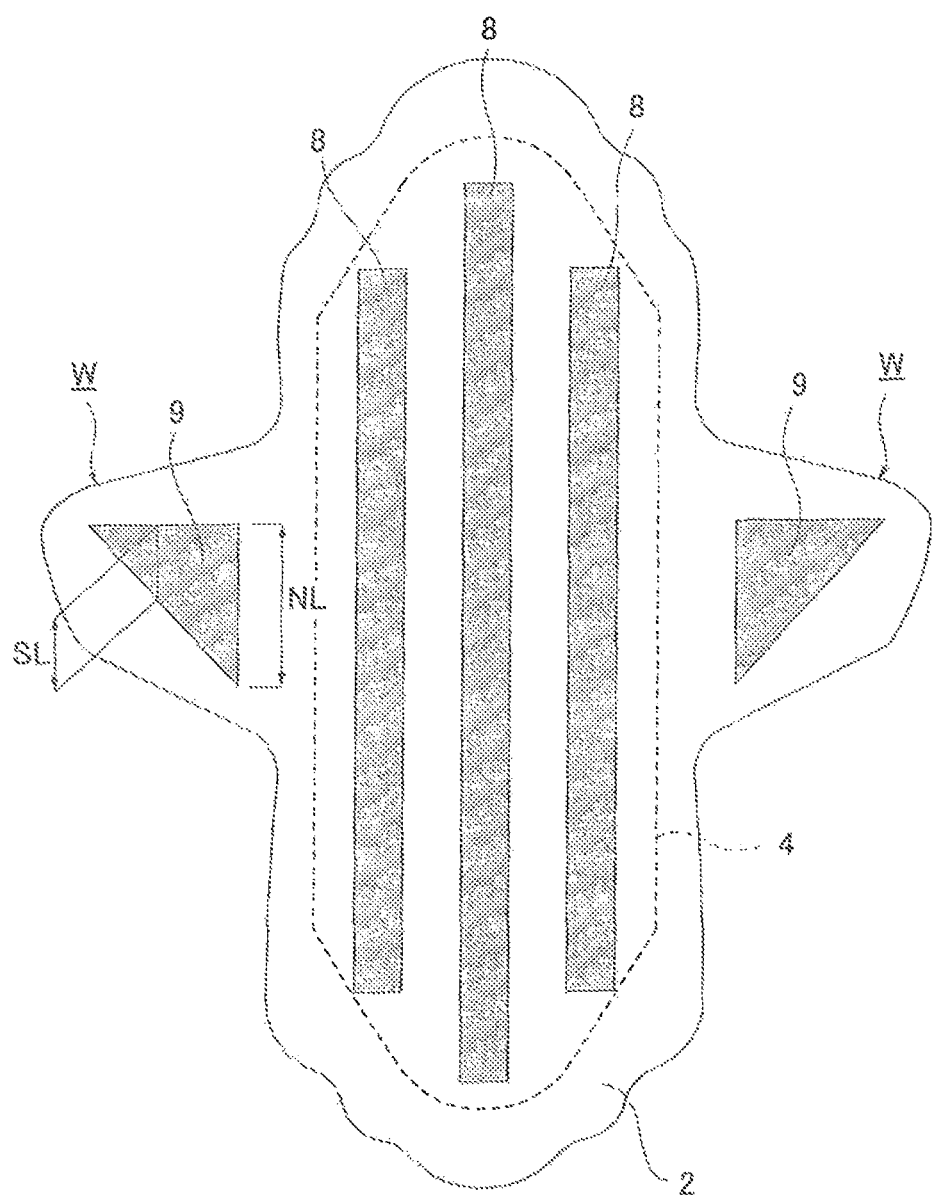
FIG. 2 is a back view thereof.
Figure 3:
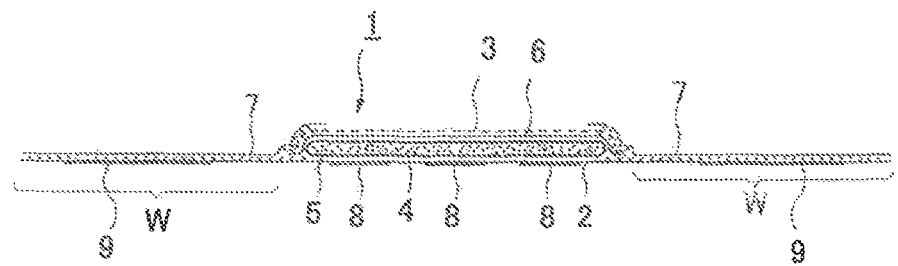
FIG. 3 is a diagram viewing from the arrow direction of line III-III shown in FIG. 1.

As shown in FIGS. 1 to 3, a sanitary napkin 1 according to the present invention is formed with a liquid impermeable back sheet 2 which is formed with a polyethylene sheet, a polypropylene sheet or the like, a liquid permeable front sheet 3 which rapidly transmits menstrual blood, vaginal discharge and the like, an absorbent member 4 which is interposed between these sheets 2 and 3 and which is formed of cotton-like pulp, synthetic pulp or the like, crepe paper 5 which surrounds the absorbent member 4 in order to retain the shape of the absorbent member 4 and to enhance diffusivity, a second sheet 6 which is interposed between the liquid permeable front sheet 3 and the crepe paper 5 and which is formed of a hydrophilic nonwoven fabric and side nonwoven fabrics 7 which are formed on both side portions of the surface along a longitudinal direction. Around the absorbent member 4, in the upper and lower end edge portions thereof, the outer edge portions of the liquid impermeable back sheet 2 and the liquid permeable front sheet 3 are joined by an adhesive such as a hot melt or an adhesive means such as a heat seal, and in both side edge portions thereof, the liquid impermeable back sheet 2 and the side nonwoven fabrics 7 extending laterally as compared with the absorbent member 4 are joined by an adhesive such as a hot melt or an adhesive means such as a heat seal.

The structure of the sanitary napkin 1 will further be described in detail below.

As the liquid impermeable back sheet 2, a sheet member, such as an olefin-based resin sheet such as polyethylene or polypropylene, which has at least a water shielding property is used, and moreover, a laminate nonwoven fabric in which a nonwoven fabric is stacked in layers on a polyethylene sheet or the like, a nonwoven fabric sheet in which a waterproof film is interposed to practically acquire liquid-impermeability (in this case, the waterproof film and the nonwoven fabric form the liquid impermeable back sheet) and the like can be used. In recent years, in terms of dampness prevention, a sheet which has moisture permeability tends to be used. The water shielding and moisture permeable sheet member is a microporous sheet that is obtained by melting and kneading an inorganic filler in an olefin-based resin such as polyethylene or polypropylene to mold a sheet and stretching it in a uniaxial or biaxial direction.

As the liquid permeable front sheet 3, a porous or non-porous nonwoven fabric, a porous plastic sheet or the like is preferably used. Examples of the material fiber of the nonwoven fabric can include the synthetic fibers of olefins such as polyethylene and polypropylene, polyesters, polyamides and the like, regenerated fibers such as rayon and cupra and natural fibers such as cotton, and nonwoven fabrics obtained by appropriate processing methods such as a spun lace method, a spun bond method, a thermal bond method, a melt-blown method and a needle punch method can be used. Among these processing methods, the spun lace method is excellent in flexibility and drapability, and the thermal bond method is excellent in bulkiness and softness. Various types of embosses are provided from the side of the upper surface of the liquid permeable front sheet 3, thus the retention of a body fluid is facilitated and the efficiency of absorption is enhanced, with the result that it is preferable to prevent side leakage.

The absorbent member 4 interposed between the liquid impermeable back sheet 2 and the liquid permeable front sheet 3 is formed with, for example, fluff-shaped pulp and a water-absorbent polymer. The water-absorbent polymer is mixed in the pulp of the absorbent member as, for example, a granular powder. Examples of the pulp described above include chemical pulps which are obtained from wood and pulps which are formed of cellulose fibers such as dissolving pulp and artificial cellulose fibers such as rayon and acetate, and as compared with hardwood pulp, softwood pulp having a long fiber length is preferably used in terms of function and price. When the crepe paper 5 surrounding the absorbent member 4 is provided as this example, the crepe paper 5 is consequently interposed between the liquid permeable front sheet 3 and the absorbent member 4, and thus a body fluid is rapidly diffused by the crepe paper 5 excellent in absorbability and the menstrual blood thereof and the like are prevented from being folded back.

Examples of the second sheet 6 formed with a hydrophilic nonwoven fabric interposed between the liquid permeable front sheet 3 and the crepe paper 5 can include the synthetic fibers of olefins such as polyethylene and polypropylene, polyesters, polyamides and the like, regenerated fibers such as rayon and cupra and natural fibers such as cotton, and nonwoven fabrics obtained by appropriate processing methods such as a spun lace method, a spun bond method, a thermal bond method, a melt-blown method and a needle punch method can be used. In order to provide hydrophilicity, a compound having a hydrophilic group may be used in the polymerization to make the polymer of a synthetic fiber, for example, an oxidation product of polyethylene glycol may be used in polymerization, the surface of the fibers may be treated with a metal salt such as stannic chloride, partially dissolving the surface to create porosity and depositing a hydroxide of the metal or the like; the synthetic fiber is swollen or made porous, with the result that it is possible to provide hydrophilicity by the application of capillarity.

On both side portions on the side of the surface of the sanitary napkin 1, along the longitudinal direction and over the substantially entire length of the napkin 1, the side nonwoven fabrics 7 are provided, and parts of the side nonwoven fabrics 7 are extended laterally, and the wing-shaped flaps W are formed with parts of liquid impermeable back sheet 2 likewise extended laterally. The wing-shaped flaps W will be described in detail later.

As the side nonwoven fabric 7, from the viewpoint of a function considered to be important, a water-repellent nonwoven fabric or a hydrophilic nonwoven fabric can be used. For example, when the function of preventing the osmosis of menstrual blood, vaginal discharge and the like or enhancing its texture is considered to be important, a water-repellent nonwoven fabric coated with a silicon-based, paraffin-based or alkyl chromic chloride-based water repellent or the like is preferably used. When the absorbability of menstrual blood and the like in the wing-shaped flaps W is considered to be important, for example, a hydrophilic nonwoven fabric is used in which.

As shown in FIG. 2, on the non-skin contact surface of a main body part where the absorbent member 4 is interposed between the liquid permeable front sheet 3 and the liquid impermeable back sheet 2, a plurality of strips of, that is, in the example shown in the figure, three strips of main body displacement prevention adhesive layers 8 are formed by an appropriate coating pattern in order to perform the fixation to the underwear, and these main body displacement prevention adhesive layers 8 are covered with an unillustrated main body separating material. On the surfaces of the wing-shaped flaps W on the side of the liquid impermeable back sheet 2, wing displacement prevention adhesive layers 9 are formed, and the wing displacement prevention adhesive layers 9 are covered with an unillustrated wing separating material. Preferably, with respect to the separating materials, the main body separating material and the wing separating material arranged in a transverse direction are joined at an intersection portion, and thus the separating materials can be removed by one separation operation. In an individually packed state, the wing-shaped flaps W may be folded back to the side of the liquid permeable front sheet 3, that is, may be subjected to so-called belly folding or may be folded back to the side of the liquid impermeable back sheet 2, that is, may be subjected to so-called back folding. As the separating material covering the wing displacement prevention adhesive layers 9, instead of the one separating material, the separating material may be separated into left and right portions.

As the separating material, paper or plastic sheet can be used in which a contact surface to the displacement prevention adhesive layers 8 and 9 is coated with or coated by spraying with a mold release processing solution such as a silicone resin, a fluorine resin or a tetrafluoride ethylene resin and is subjected to mold release processing.

As the adhesive that forms the displacement prevention adhesive layers 8 and 9, for example, an adhesive whose main component is any one of a styrene-based polymer, a tackifier and a plasticizer is preferably used. Examples of the styrene-based polymer include a styrene-ethylene-butylene-styrene block copolymer, a styrene-butylene-styrene block copolymer and a styrene-isobutylene-styrene copolymer, and only one type thereof may be used or a polymer blend of two or more types may be used. Among them, since thermal stability is satisfactory, the styrene-ethylene-butylene-styrene block copolymer is preferable. As the tackifier and the plasticizer, a tackifier and a plasticizer which are solid at room temperature can be preferably used, and examples of the tackifier include a C5-based petroleum resin, a C9-based petroleum resin, a dicyclopentadiene-based petroleum resin, a rosin-based petroleum resin, a polyterpene resin and a terpene phenol resin, and examples of the plasticizer include monomeric plasticizers such as tricresyl phosphoric acid, dibutyl phthalate and dioctyl phthalate and polymeric plasticizers such as a vinyl polymer and polyester.

[Wing-Shaped Flap W]

Figure 4:
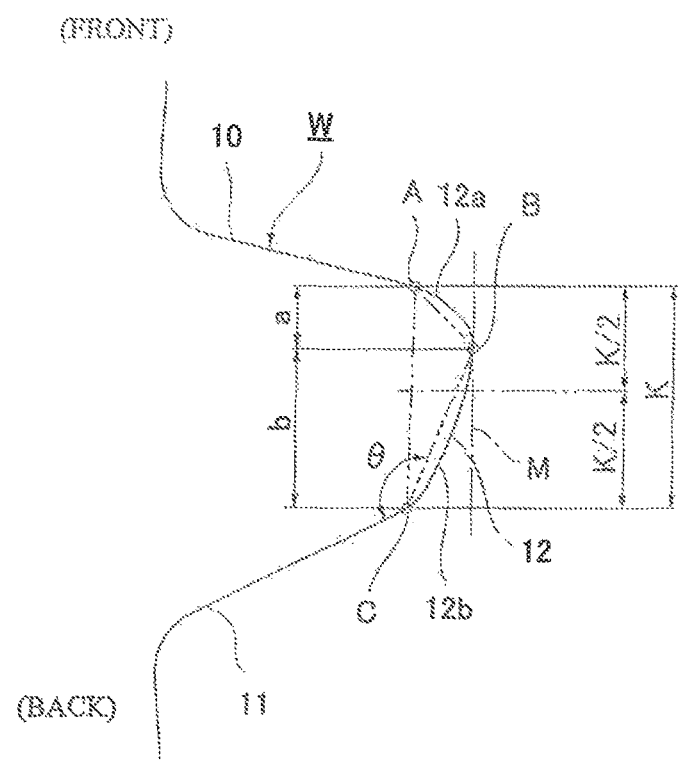
FIG. 4 is a plan view of an enlarged main portion of a wing-shaped flap W.

Specifically, as shown in FIG. 4, the wing-shaped flap W forms an outline shape that is formed with a front side outline 10 which is extended outward from the main body part, a back side outline 11 which is extended outward from the main body part and a tip end side outline 12 which connects the front side outline 10 and the back side outline 11.

The tip end side outline 12 is formed with a tip end side outline front portion 12a which is extended outward from an end portion A of the front side outline 10 and a tip end side outline back portion 12b which is extended outward from an end portion C of the back side outline 11. As shown in FIG. 4, the end portion A of the front side outline 10 and the end portion C of the back side outline 11 indicate, when the front side outline 10 or the back side outline 11 is formed with a straight line, a part which is separated from the straight line, indicate, when the front side outline 10 or the back side outline 11 is formed with a wavy line made by a combination of a convex curve and a concave curve, a part which is separated from a tangent connecting the apex portions of the convex curve, and indicate, when the front side outline 10 or the back side outline 11 is formed with a curve, a part where a curve is started whose radius of curvature is rapidly decreased or whose center of curvature's position is rapidly changed.

An intersection B between the tip end side outline front portion 12a and the tip end side outline back portion 12b forms an outermost side end portion in the width direction of the wing-shaped flap W. The outermost side end portion in the width direction of the wing-shaped flap W refers to a tip end part in the width direction where the outline of the wing-shaped flap W is tangent to a line M in the longitudinal direction of the napkin on the outermost.

The intersection B is located on the front side of the napkin as compared with the center point (K/2) of a length K in the longitudinal direction of the napkin between the end portion A of the front side outline 10 and the end portion C of the back side outline 11. In other words, as shown in FIG. 4, when it is assumed that the lengths of AB and BC in the longitudinal direction of the napkin are a and b, respectively, a<b preferably holds true, and the intersection B is more preferably provided in a position where a:b is about 1:1.5 to 1:3.

When the shape which satisfies the conditions described above is schematically shown, as shown in FIG. 4, on the outer side of a line AC connecting the end portion A of the front side outline 10 and the end portion C of the back side outline 11, an outer bulging portion is formed which is displaced to the front side of the napkin with respect to the center of the line AC and in which an outer end portion B in the width direction of the wing-shaped flap W is its apex. The outer bulging portion has a triangle ABC as a basic form, and each of the side AB and the side BC is formed with a curve, a straight line or a combination thereof. In the example shown in the figure, the each of the side AB and the side BC is formed with a curve which is bulged outward. The outer bulging portion is formed, and thus on the outer side with respect to the end portion C of the back side outline 11, the tip end side outline back portion 12b extending outward and obliquely forward is provided toward an outer side end portion B in the width direction of the wing-shaped flap W.

The wing-shaped flap W is shaped as described above, and thus when the wing-shaped flap W is folded back at the time of the fitting of the napkin, it is possible to fold the wing-shaped flap W by putting a hand along substantially the entire width of the wing-shaped flap W, with the result that even the tip end side can be securely fixed to the underwear. Specifically, as will be described in detail later, although when the wing-shaped flap W is folded back, as shown in FIG. 8(B), an operation of moving the hand is performed by putting the back side outline 11 of the wing-shaped flap W from a base end side along the direction of the tip end side, in the case of a conventional wing-shaped flap W having an isosceles trapezoid shape, the length of the back side outline from the wing base end side to the tip end side is short, furthermore the tip end side outline is formed with a straight line substantially parallel to the longitudinal direction of the napkin and thus such a structural disadvantage is formed that it is difficult to perform the operation of putting the hand therealong to the tip end side outline. Hence, it is likely that the wing-shaped flap cannot be accurately folded back in a proper return position, and that the wing-shaped flap cannot be securely fitted to the underwear. In particular, the tip end of the wing-shaped flap along which it is difficult to put the hand is disadvantageously and easily peeled.

Hence, in the present invention, as shown in FIG. 8(B), when the wing-shaped flap W is folded back with the hand while an operation of moving the hand forward along the back side outline 11 and the tip end side outline back portion 12b is being performed, the wing-shaped flap can be accurately fitted in a proper state, the hand can be put therealong to the tip end of the wing-shaped flap and the wing-shaped flap is formed in a wing shape in which the wing-shaped flap can be securely fitted to the underwear.

As shown in FIG. 4, an angle θ formed by a straight line BC (the tip end side outline back portion 12b) connecting the end portion C of the back side outline 11 and the outermost side end portion B in the width direction of the wing-shaped flap W and the back side outline 11 preferably falls within about a range of $115°≤θ≤160°$. The tip end side outline back portion 12b is provided such that the angle θ falls within this angular range, and thus the wing-shaped flap is easily fitted by putting the hand therealong continuously from the back side outline 11 to the tip end side outline back portion 12b.

As shown in FIG. 4, the tip end side outline front portion 12a and the tip end side outline back portion 12b can be formed with a curved line which is bulged outward. The tip end side outline back portion 12b is formed with the curved line, and thus the outline from the end portion C of the back side outline 11 to the outermost side end portion B in the width direction of the wing-shaped flap W is connected by a smooth curve, and thus it is possible to smoothly put the hand therealong from the back side outline 11 to outermost side end portion B in the width direction of the wing-shaped flap W, with the result that the fitting operation is easily performed. The tip end side outline front portion 12a is formed with the curved line, and thus the part from the end portion A of the front side outline 10 to the outermost side end portion B in the width direction of the wing-shaped flap W is connected by the smooth curve, with the result that it is possible to prevent this part from being separated.

As shown in FIG. 4, the back side outline 11 is preferably formed with a straight line or a curve slightly bulged outward so that the hand can be easily put therealong when the wing-shaped flap W is folded back. If the back side outline 11 is formed with a wavy line or a curve significantly bulged outward, this is not desirable because when the hand is moved along the back side outline 11, a finger is caught in the projections and recesses of the wavy line or the curve.

Figure 5:
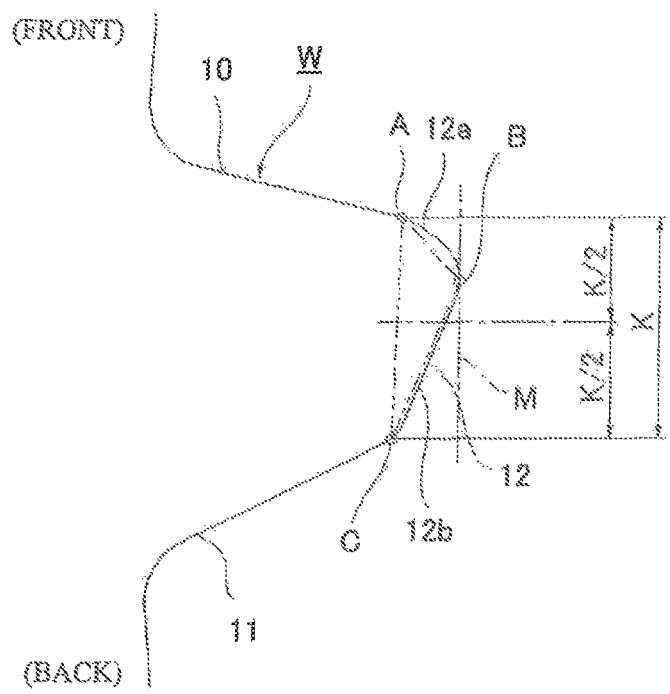
FIG. 5 is a plan view showing a variation of the wing-shaped flaps W according to the present invention.

A variation of the wing-shaped flap W will then be described. As shown in FIG. 5, the tip end side outline back portion 12b can be formed with a straight line. In this way, the hand is easily and linearly put along the tip end side outline back portion 12b. In the connection part (C) between the tip end side outline back portion 12b and the back side outline 11, the connection is preferably made with a gentle curve such that a corner portion is prevented from being formed.

Figure 6:
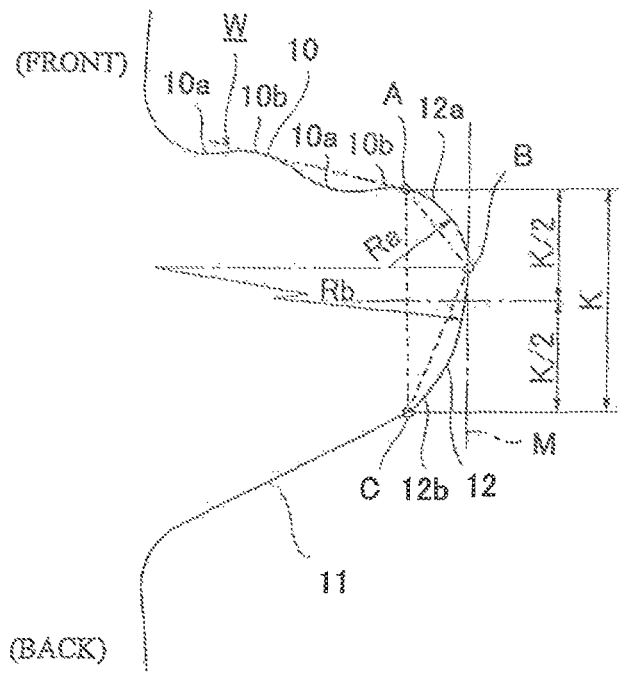
FIG. 6 is a plan view showing a variation of the wing-shaped flaps W according to the present invention.

In a second variation, as shown in FIG. 6, the front side outline 10 can be formed with a wavy line, a curve or a combination thereof. The front side outline 10 is formed in such a shape, and thus as compared with a case where the front side outline 10 is formed with a straight line, the rigidity of the front side of the wing-shaped flap W is enhanced, and thus when the wing-shaped flap W is folded back, it can be fitted without a wrinkle and a crease. The wavy line is formed with a combination of convex curves 10b and concave curves 10a, and the convex curves 10b and the concave curves 10a are alternately arranged, and thus one or more of convex portions and one or more of concave portions are formed with respect to a line passing through the center portion of the convex curve 10b and the concave curve 10a. The curve is preferably a curve which is bulged outward but may be a curve which is bulged inward.

As shown in FIG. 6, when the tip end side outline front portion 12a is formed with a curved line which is bulged outward, the front side outline 10 is formed with a wavy line, a curve or a combination thereof, and thus the part from the front side outline 10 to the tip end side outline front portion 12a is provided in a shape in which the wavy line or the curve is continuous, with the result that an effect produced by forming the front side outline 10 with the wavy line or the like is more achieved.

The outline of the wing-shaped flap W shown in FIG. 6 will be described in more detail. The front side outline 10 is formed with a wavy line made of the convex curves 10b and the concave curves 10a, the concave curve 10a is provided so as to be extended from a curve which is tangent to the side edge of the main body part, on the outer side thereof, the convex curve 10b and the concave curve 10a are provided and furthermore an arc that is bulged outward of the tip end side outline front portion 12a is started so as to be extended from the apex portion (A) of the convex curve 10b provided outward thereof and is extended to a point B. The tip end side outline front portion 12a is formed with an arc having a single radius of curvature Ra, and the center of curvature thereof is located on a line of the napkin in the width direction passing through the point B. The radius of curvature Ra is preferably about 10 to 20 mm. On the other hand, the back side outline 11 is formed with a straight line connected between the side edge of the main body part and a curve, the end portion C serves as a boundary and the curve which is bulged outward of the tip end side outline back portion 12b is started and is extended to the point B. The tip end side outline back portion 12b is formed with a combination of arcs having a plurality of radiuses of curvature, and has, in a connection part to the point B, an arc component whose center of curvature is located on the line of the napkin in the width direction passing through the point B and which has a radius of curvature Rb. The radius of curvature Rb is preferably about 70 to 120 mm.

Figure 7:
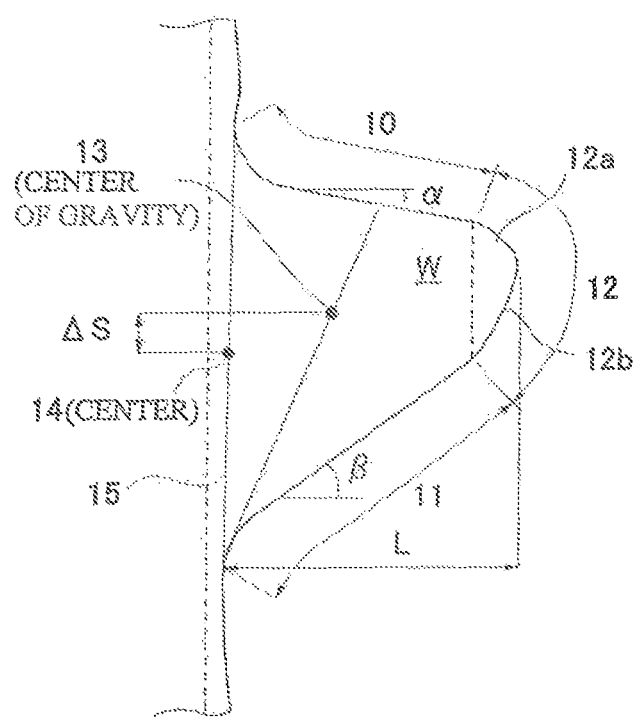
FIG. 7 is a schematic view showing the planar shape of the wing-shaped flap W.

Preferably, in the sanitary napkin 1, as shown in FIG. 7, the shape of the wing-shaped flap W is set such that an angle β formed by a line of the sanitary napkin 1 in the width direction and the back side outline 11 is greater than an angle α formed by the line of the sanitary napkin 1 in the width direction and the front side outline 10, and the center of gravity 13 in the wing-shaped flap W is displaced to the front side by ΔS with respect to a center point 14 of a joint line 15 of the root and the main body part of the wing-shaped flap W. The front side outline 10, the back side outline 11 and the tip end side outline 12 does not need to be formed with a straight line, and may be formed with a wavy line, a curve or a combination thereof. In this case, as the angles α and β, gradients formed by the center lines of these wavy or curve outlines are preferably taken.

Preferably, the angle α formed by the line of the sanitary napkin 1 in the width direction and the front side outline 10 is set at about 0 to 20°, and the angle β formed by the line of the sanitary napkin 1 in the width direction and the back side outline 11 is set at about 20 to 45°. In this case, an angle difference between the angle α formed by the line of the sanitary napkin 1 in the width direction and the front side outline 10 and the angle β formed by the line of the sanitary napkin 1 in the width direction and the back side outline 11 is preferably set equal to or more than 25°. When the angle difference is equal to or more than 25°, a sufficient eccentric distance ΔS can be acquired, and even when as will be described later, the wing-shaped flap W is folded back by the hand while an operation of moving the hand to the front side is being performed, the wing-shaped flap can be securely fitted in a proper state.

Figure 10:
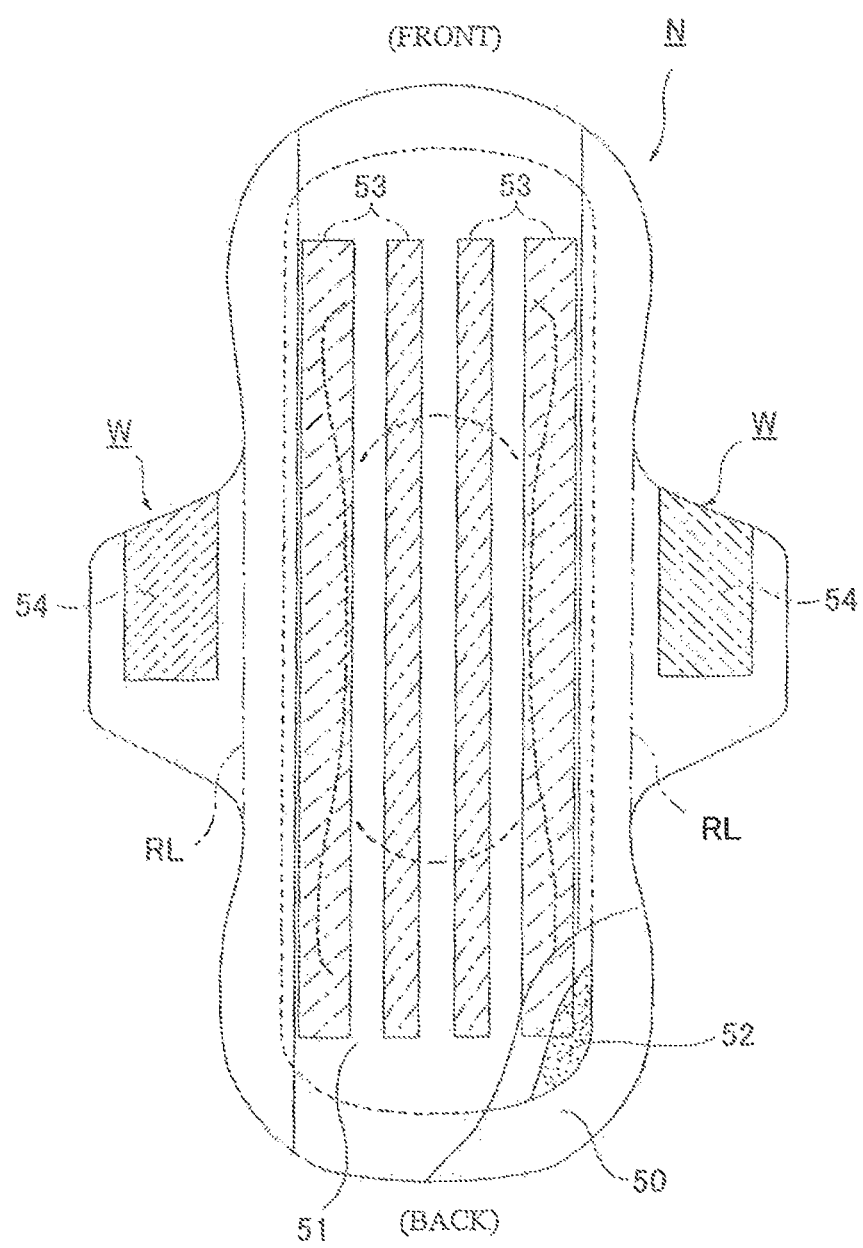
FIG. 10 is a development view of a conventional sanitary napkin N.
Figure 11:
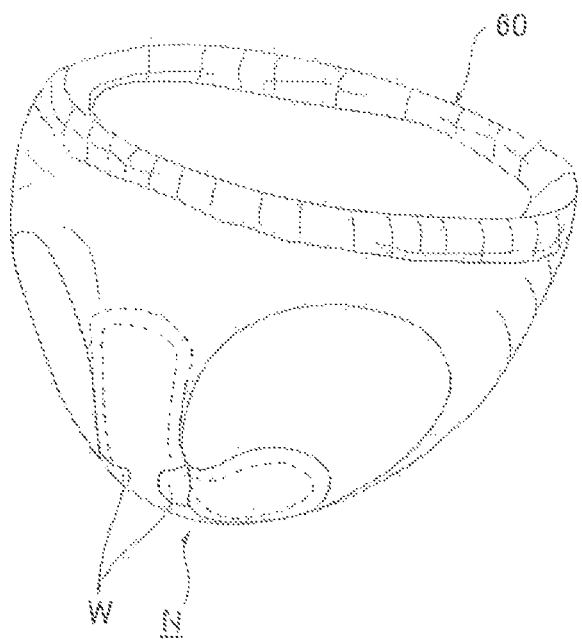
FIG. 11 is a diagram showing a state in which it is fitted.

The wing-shaped flap W is formed so as to have the outline shape described above, and thus for example, advantages can be produced in which failures such as the adhesion of adhesives and erroneous adhesion are prevented from occurring in the wing-shaped flap W, in which it is possible to easily and accurately fold back and adhere the wing-shaped flap in a proper return position and in which it is possible to securely fit the wing-shaped flap W to the underwear by putting the hand therealong to the tip end of the wing-shaped flap W. This point will be further described in detail by comparison with the conventional wing-shaped flap W (see FIG. 10) having an isosceles trapezoid shape.

First, when a woman fits the sanitary napkin 1 to panties 20 while sitting on a toilet bowl or the like, since the fitting is performed with the panties 20 lowered, as shown in FIG. 8, the operation of fitting the sanitary napkin 1 is performed on the front side with respect to the body.

Figure 8A:
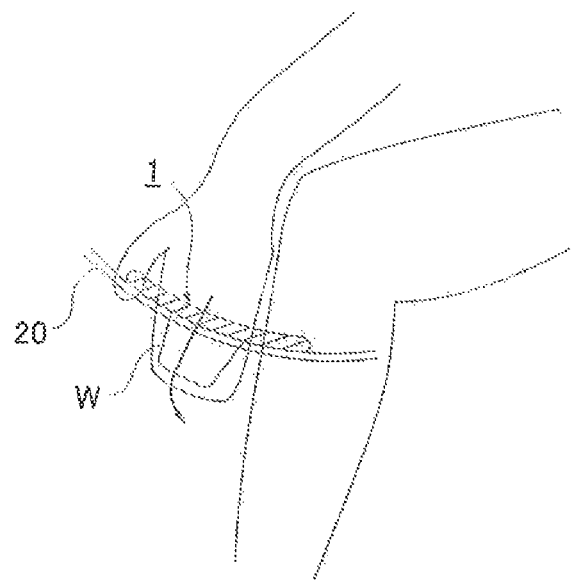
FIG. 8(A) shows a procedure for fitting the napkin in the case of a conventional wing-shaped flap.
Figure 8B:
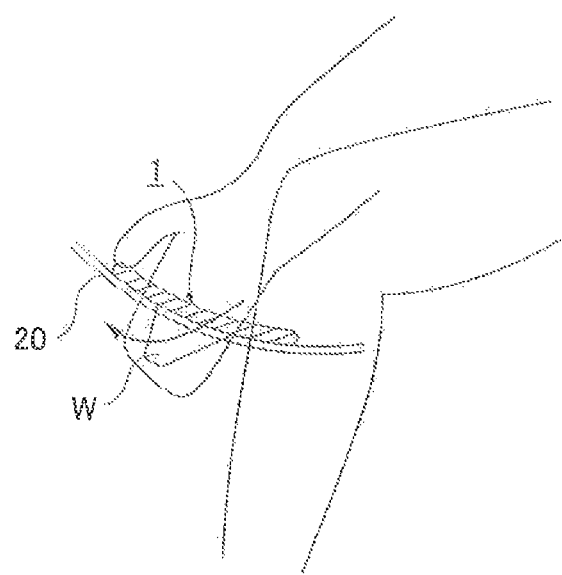
FIG. 8(B) shows a procedure for fitting the napkin in the case of the wing-shaped flap according to the present invention.

As shown in FIG. 8(A), the conventional wing-shaped flap W having an isosceles trapezoid shape has a structure in which the fitting cannot be satisfactorily performed unless the wing-shaped flap is folded back in a direction immediately therebelow from a state where the hand is put on both sides of the napkin. However, for example, a failure occurs in which since the position of the fitting is located on the front side with respect to the body, an operation (FIG. 8(B)) of moving the hand to the front side is carelessly performed, only part of the wing-shaped flap is folded back, the adhesives are adhered to each other and thus a wrinkle or a raised portion is produced or erroneous adhesion where the wing-shaped flap W is folded back at the middle to adhere to the adhesive layer is produced. The return line of the wing-shaped flap may be bent obliquely and folded back. Hence, in the present invention, as shown in FIG. 8(B), the wing shape is adopted such that even when the wing-shaped flap W is folded back by the hand while the operation of moving the hand to the front side is being performed, the wing-shaped flap can be securely fitted in a proper state and that it is possible to put the hand therealong to the tip end of the wing-shaped flap W.

Figure 9A:
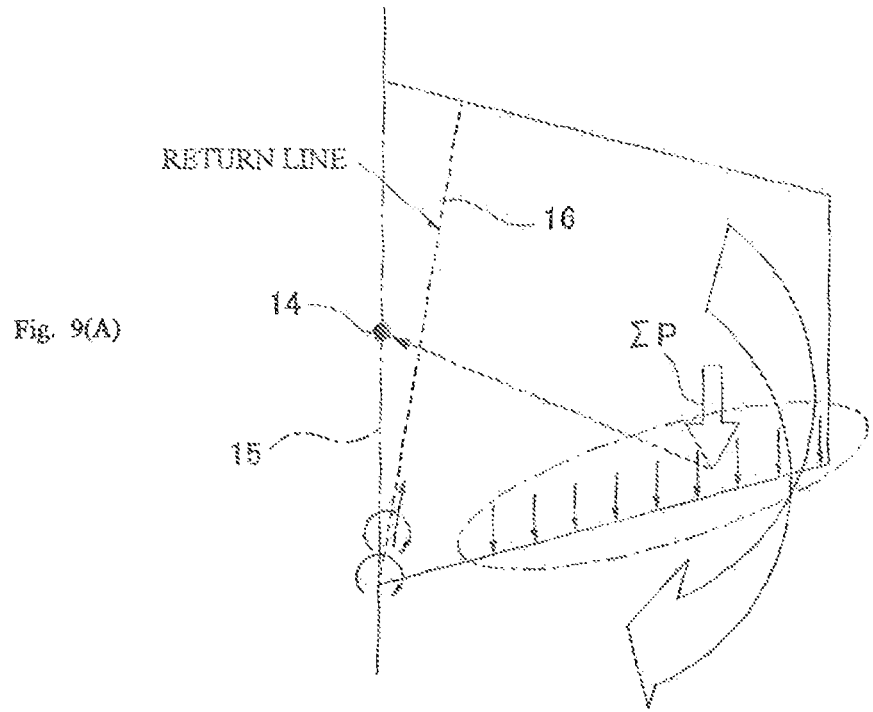
FIG. 9(A) shows a mechanism of an acting force when the wing-shaped flap W is folded back in the case of a conventional wing-shaped flap.

FIG. 9(A) is a diagram showing the mechanism of an acting force when the conventional wing-shaped flap W having an isosceles trapezoid shape is returned back. In a case where the wing-shaped flap W is folded back by the hand while the operation of moving the hand to the front side is being performed, when it is assumed that a load applied downward from the back side outline of the wing-shaped flap W to the tip end side acts and that a concentrated load ΣP is obtained by collecting the load distribution thereof, the base point of a moment produced by the concentrated load ΣP is the center point 14 of the joint line 15 in the wing-shaped flap W, a twist occurs when the wing-shaped flap W is folded back and a return line 16 gradually travelling from the base end of the back side outline 11 is inclined outward.

Figure 9B:
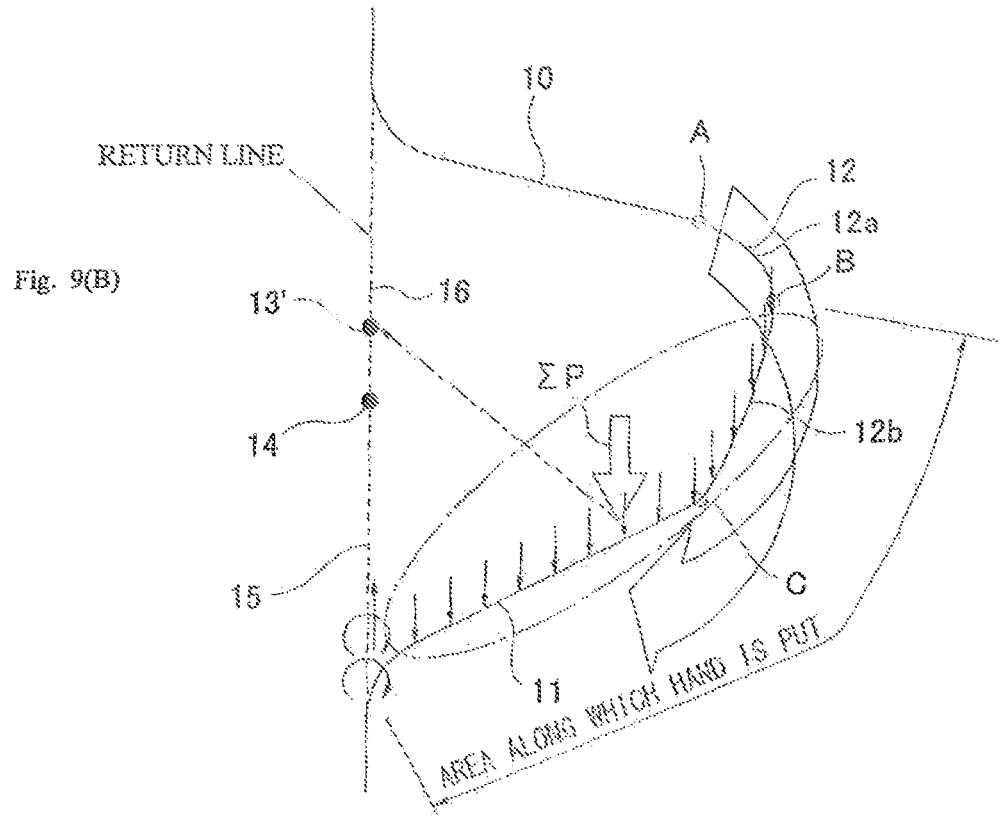
FIG. 9(B) shows a mechanism of an acting force when the wing-shaped flap W is folded back in the case of the wing-shaped flap according to the present invention.

By contrast, in the present invention, as shown in FIG. 9(B), when a load applied downward acts on the center part of the inclined back side outline 11 and that a concentrated load ΣP is obtained by collecting the load distribution thereof, the base point of a moment produced by the concentrated load ΣP is a barycenter division point 13' (division point of about 1:2 in the joint line 15), only a small amount of twist occurs when the wing-shaped flap W is folded back and thus the return line 16 gradually travelling from the base end of the back side outline 11 coincides with the joint line 15, with the result that the wing-shaped flap W is folded back in the proper return position. In the wing-shaped flap W shown in FIG. 9(B) and according to the present invention, since the wing-shaped flap W is folded back while the hand is being put along the outline of the back side of the flap from the back side outline 11 to the tip end side outline back portion 12b, the return line 16 reliably and gradually travels from the base end of the back side outline 11 toward the front side.

Since the back side outline 11 of the wing-shaped flap W is significantly inclined, failures such as the adhesion of adhesives and erroneous adhesion are prevented from occurring in the wing-shaped flap W, and the wing-shaped flap W is accurately folded back on the return line RL.

On one hand, the length L of protrusion of the wing-shaped flap W is set at 40 to 50 mm, and is preferably set longer than the half of the crotch width of the shorts 20. The length L is set longer than the half of the crotch width of the shorts 20, and thus it is possible to securely fix the shorts.

On the other hand, preferably, as shown in FIG. 2, the wing displacement prevention adhesive layer 9 provided on the side of the back surface of the wing-shaped flap W is formed in a shape in which in the width of the napkin 1 in the longitudinal direction, a tip end side SL is narrower than a base end side NL, and specifically, is formed in a substantially triangular shape, a substantially isosceles shape or an unequal isosceles shape. In this way, when the wing-shaped flap W is folded back, it is unlikely that the adhesion of adhesives and erroneous adhesion occur.

The invention claimed is:

1. An absorbent article, comprising a main body part comprising an absorbent member interposed between a liquid permeable front sheet and a liquid impermeable back sheet, and, at each side of the main body, a respective wing-shaped flap configured for wrapping a crotch part of underwear,
   wherein the wing-shaped flap is formed with a front side outline which is extended outward from the main body part, a back side outline which is extended outward from the main body part and a tip end side outline which connects the front side outline and the back side outline,
   the tip end side outline includes a tip end side outline front portion which is extended outward from the front side outline and a tip end side outline back portion which is extended outward from the back side outline, an intersection between the tip end side outline front portion and the tip end side outline back portion forms an outermost side end portion in a width direction of the wing-shaped flap and is located on a front side with respect to a center point of a length between an end portion of the front side outline and an end portion of the back side outline in a longitudinal direction of the absorbent article, and when it is assumed that a length in the longitudinal direction of the absorbent article between the end portion of the front side outline and the outermost side end portion in the width direction is a and a length in the longitudinal direction of the absorbent article between the end portion of the back side outline and the outermost side end portion in the width direction is b, the outermost side end portion in the width direction is provided in a position where a:b is 1:1.5 to 1:3,
   the front side outline is formed with a wavy line made of convex curves and concave curves, and a section from an apex portion of the convex curve provided outermost to the outermost side end portion in the width direction of the wing-shaped flap is the tip end side outline front portion, the tip end side outline front portion being formed with a curved line which is bulged outward,
   the back side outline is formed with a straight line, and a section from the end portion of the back side outline to the outermost side end portion in the width direction of the wing-shaped flap is the tip end side outline back portion, the tip end side outline back portion being formed with a curved line which is bulged outward.

2. The absorbent article according to claim 1, wherein an angle θ formed by a straight line connecting the end portion of the back side outline and the outermost side end portion in the width direction of the wing-shaped flap and the back side outline falls within a range of 115°≤θ≤160°.

3. The absorbent article according to claim 1, wherein the tip end side outline front portion is formed with an arc having a single radius of curvature, and the tip end side outline back portion is formed with a combination of arcs having a plurality of radiuses of curvature.

4. The absorbent article according to claim 1, wherein the tip end side outline front portion has the radius of curvature of 10 to 20 mm, and the center of curvature thereof is located on a line of the absorbent article in the width direction passing through the outermost side end portion in the width direction of the wing-shaped flap, and the tip end side outline back portion has, in a connection part with the outermost side end portion in the width direction of the wing-shaped flap, an arc component whose center of curvature is located on the line of the absorbent article in the width direction passing through the outermost side end portion in the width direction of the wing-shaped flap and which has a radius of curvature of 70 to 120 mm.

* * * * *